United States Patent [19]

Martin

[11] Patent Number: 5,026,284
[45] Date of Patent: Jun. 25, 1991

[54] APEX ROOT CANAL FILE

[76] Inventor: Howard Martin, 909 Pershing Dr., Silver Spring, Md. 20910

[21] Appl. No.: 156,813

[22] Filed: Feb. 17, 1988

[51] Int. Cl.$^5$ .............................................. A61C 5/02
[52] U.S. Cl. ................................................... 433/102
[58] Field of Search ................................. 433/102, 81

[56] References Cited

U.S. PATENT DOCUMENTS 4,231,738  11/1980  Riitano et al. ...................... 433/102
4,332,561  1/1982   McSpadden ......................... 433/102

Primary Examiner—Cary E. Stone
Attorney, Agent, or Firm—Walter G. Finch

[57] ABSTRACT

In root canal preparation, there is provided a smooth sided pilot ended endodontic K-type file, a K-type reamer file, a H-type Hedstroem file, an S-type file, and a R-type file (rhomboid), with the safe end of the instrument or file measured from D1 from 1–3 mm before the cutting edges are developed on all types of endodontic cutting instruments and on all sizes from 06–140.

The smooth sided pilot end of the apex file can be incrementally increased based upon the increasing size of the instruments. For example, #15=1 mm smooth sided pilot end, #20=2 mm safe end, #25=3 mm smooth sided pilot end, etc. This is to be used for ease with the step back preparation technique. The smooth sided pilot ended apex file instrument has the ability to act as pathfinder into the root canal without damaging the apex portion during this phase.

The smooth sided pilot ended endodontic file of this invention avoids forcing debris and filling material out the apex and creates a proper apical stop of proper retention and resistance. The smooth sided pilot ended endodontic file of this invention is necessary to achieve the critical phase of root canal preparation.

9 Claims, 2 Drawing Sheets

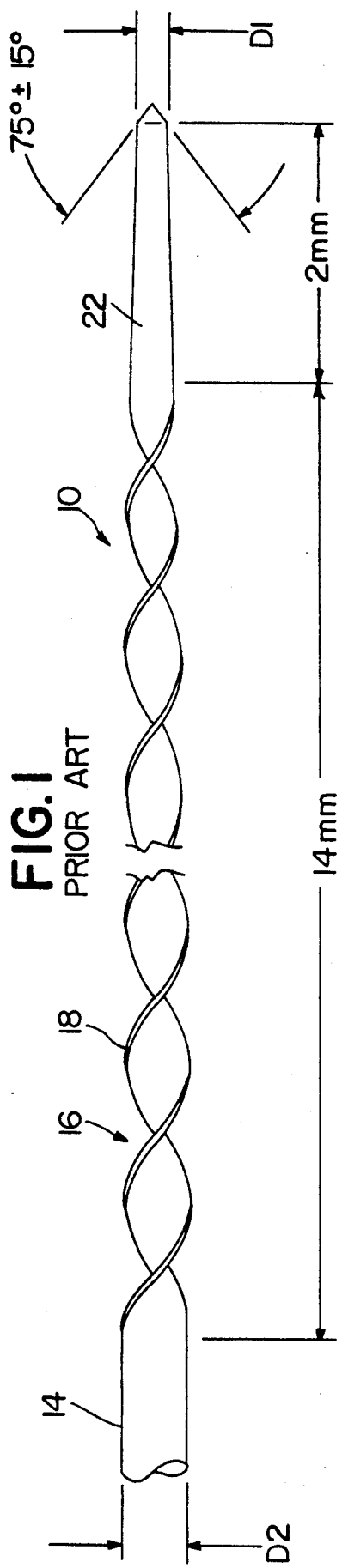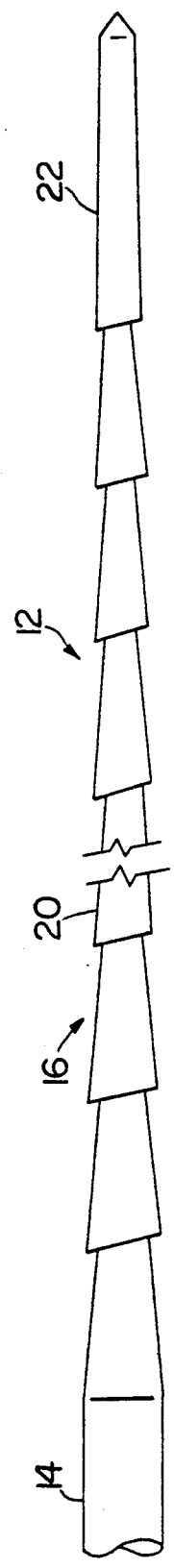
FIG.1 PRIOR ART
FIG.2 PRIOR ART

APEX ROOT CANAL FILE

BACKGROUND AND SUMMARY OF THE INVENTION

This invention relates to dental devices, and more particularly to endodontic type files for use in preparing root canals.

The success of root canals is based upon proper root canal enlargement and controlled root canal filling. A well shaped root canal presents a gradually tapering cone with the narrowest part directed apically. This requires careful preparation of the apical few millimeters. The desired apical extent of root canal preparation is the dentinocemental junction. This is now accepted to be at least 1-2 mm short of the radiographic apex.

An apical preparation in solid dentin acts as a matrix to pack the root canal filling material against. If the apical constriction is destroyed or overprepared, it will be very difficult to control the root canal filling terminus. Because the root canal file/reamer/Hedstroem/S type and rhomboid shape file (R-type) instruments come to a point with a side cutting edge, the canal preparation in solid dentin also comes to a point with dentin removed on the side.

Preparation of the root canal is accomplished by mechanical instruments that are used to enlarge the root canal by physically removing internal root canal tooth structure, dentin, but the instruments do not properly shape the canal.

Examples of these instruments are the K-type file, K-type reamer, Hedstroem file (H type) and (S type) and rhomboid shape file (R type). They are standardized instruments following ISO guidelines. K type files are twisted to create the cutting flutes. They are tapered and pointed metal instruments with a tight spiral cutting edge so that the cutting occurs on either a push or pull stroke. These files enlarge the root canal by rotational cutting or abrasive action.

THe difference between a K file and K reamer is the number of cutting flutes per millimeter of length.

H type (Hedstroem) files are made by machine grinding the flutes of the file into the metal stock. The angle is close to perpendicular to the shaft central axis while newer forms are less than perpendicular for increased cutting efficiency on the withdrawal stroke. These files are also pointed and incremental instruments getting larger as they increase in umber size. S is a combination of K file and H type.

The ANSI, ADA, and ISO standards for these instruments have been determined. Tip angle is 75 ±15, taper is 0.02 mm/mm, cutting length is 16 mm. The flutes blades of these instruments are carried within 0.1 mm of the tip of the instruments(D1).

With these instruments, hand operated, the dentist attempts to accomplish the canal preparation for enlargement and precise filling. The goal of root canal preparation is to attain an apical terminus kept as small as practical in order to achieve more effective packing with greater condensation control based upon an effectively prepared apical seat, collar, matrix and stop.

This leads to minimal risk of pushing material beyond the apical foramen into the surrounding tissues of the jaws. This is best achieved by creating the narrowest part of a tapering cone at the apex of root canal preparation. The wider portion is necessary coronally in order to clean, irrigate, remove debris and allow for insertion of the filling material and filling instruments. The apical foramen can be tranported, moved or lost during canal preparation either externally or internally. External transportation occurs when instrumentation is carried to or inadvertently beyond the terminus of the root canal due to misplacement or overfilling. External transportation causes a tear drop or ripping of the apical foramen.

Internal transportation occurs when work is being done short of the proper apical length. This causes ledges, perforations, or transportation.

The apical foramen must be kept patent by constant reprobing with instruments otherwise there is a tendency for dentin shavings from these type of instruments to block the canal apex. All these designed instruments thereby create great difficulties in controlled filling leading to potential failure of the root canal treatment.

Another object of the apical preparation is to create the apical stop that allows for control of the root canal filling material. With continual filing, the apex is inadvertently enlarged leading to loss of control, more debris passing through, ripping. This can lead to an inflammatory process around the apex. It also complicates the condensation and compaction of the root canal filling during the obturation phase.

Various techniques utilizing the presently existing designed K-files, K-reamers, H-file Hedstroem, S-files and R-files have been developed and described in order to maintain the apex and yet enlarge, clean and shape the canal. The traditional method has been to file to the apex and twist the instrument in order to create the apical matrix and stop. This is done by increasing sequential placement of all instruments to the apex. This has been the prime method for over 40 years and still is taught in dental schools. This however does apical damage and destroys the anatomic apex.

A refinement has been the step-back or serial technique. The small sized files go the apex; incrementally larger sizes are used short of the apex and the largest even shorter from the apical foramen. Between successive sizes, the operator recapitulates with small sized instruments. Recapitulation is the sequential reentry and reuse of previously employed instruments, usually of smaller sizes, within the root canal.

However, the instruments are still either fluted or barbed and there is continual risk of altering the apex while recapitulation is being accomplished. The larger cutting instruments also pack debris causing blockage necessitating some form of recapitulation. This concept is valid except for the unnecessary recutting of the previously worked apex.

The apex file of this invention is a safe-ended K-type file, reamer, or H type (Hedstroem), S-file, and R-type file (rhomboid). The key to the apex is smooth sided pilot, which is also called the "safe end". The safe end is a smooth sided pilot with a pointed tip. The smooth sides extend 0.5 to 3 mm. from the tip of the instrument, (D1). The fluting or barbs start. 5-3 mm from, the ISO tip. The safe end tip allows the operator to penetrate to the apex, without cutting or abrasive action laterally, thereby preserving the prepared apical form without further alteration and also develops the apical matrix, stop collar, at the same time.

One method for accomplishing the apical preparation is the step-back technique. The series of files used in this technique may increase sequentially both in length and the diameter of the smooth sided probe (safe end).

It is to be noted that with respect to the step-back series of files, the safe-end portion may be more tapered than the ISO portion or be of smaller diameter than the cutting portion. This is to facilitate penetration of the original working distance within the root canal preparation.

Therefore, the safe-end in the step-back series may require either a greater taper or a step down in diameter from the cutting portion to the smooth sided pilot portion. Meaning, that file member becomes larger than would be within the usual ISO specifications for a file, with the same size tip diameter.

For example, a #35 safe-end file in the step-back series could have the safe-end section equivalent to a #25 size in the safe-end while the fluted section will still be equivalent to a #35. It is most likely that all safe-ends within the step-back series would not go above a #25 taper within the safe-end.

Length control is more easily maintained with this apex file of the present invention even under less than accurate conditions. The cutting ability of the larger apex file being several millimeters short of the instrument tip will create automatically an apical step, collar, matrix, stop, superior to the actual prepared foramen enabling the root canal filling to bind at that point and be easier to control at the apical portion.

Using the apical files of this invention, better condensation and more controlled compaction pressure can be accomplished by this step/collar preparation in the apical area. This enhances filling and control of the critical obturation phase procedure.

This creates an apical matrix collar at the narrowest aspect of the canal so as to allow easier preparation of the apex prior to filling the canal. It avoids the problem of over preparation cutting due to the safe end. This newly prepared apical matrix collar is actually a proper cavity preparation which gives the retention and resistance form to the apical preparation.

In order to avoid forcing debris and filling material out the apex and in order to create a proper apical stop of proper retention and resistance, a correctly designed instrument is necessary to achieve this critical phase of root canal preparation. This type of instrument is presently not available. It is the purpose of the apex file of this invention to solve the problem.

SUMMARY

A safe ended endodontic K-type file, K-type reamer, H-type Hedstroem instrument, S-type file and R-type file (rhomboid) is provided. The safe end is a smooth sided pilot with a pointed tip. The safe end of the instrument safe end of the instrument measured from D1 will be from 0.5 mm before the cutting edges are developed on all types of endodontic cutting instruments and on all sizes from 05-40. The safe end of the apex file can be incrementally increased based upon the increasing size of the instruments; For example, #15=0.5 mm safe end, #20=1 mm safe end, #25=1.5 mm safe end, etc. (This is to be used for ease with the step back preparation technique).

Another aspect of the safe ended apex file instrument is its ability to act as pathfinder into the canal without damaging the apex portion during this phase.

OBJECTS OF THE INVENTION

One of the major objects of this invention is to provide a new design of a safe ended apex file for a root canal K-file reamer, H-type, S-type endodontic instrument, and R-type file (rhomboid).

It is an object of this invention to provide a safe ended endodontic K-type file, K-type reamer, H-type Hedstroem instrument, S-type file and R-type (rhomboid) file for root canal use.

Still another object of this invention is to provide a safe end of an apex file which is measured from a fixed point will be from one-half (0.5) to three (3) millimeters before the cutting edges are developed on all types of endodontic cutting instruments and on all sizes.

And even another object of this invention is to provide the safe end of the file which can be incrementally increased based upon the increasing size of the instruments used in connection with preparing root canals.

Still even another object of this invention is to provide a safe ended apex type file instrument which has the ability to act as a pathfinder into the canal without damaging the apex portion during this preparation phase.

BRIEF DESCRIPTION OF THE DRAWINGS

FIG. 1 is a drawing of a side view of a prior art file;
FIG. 2 is a drawing of a side view of a second prior art file.

Figure 3:
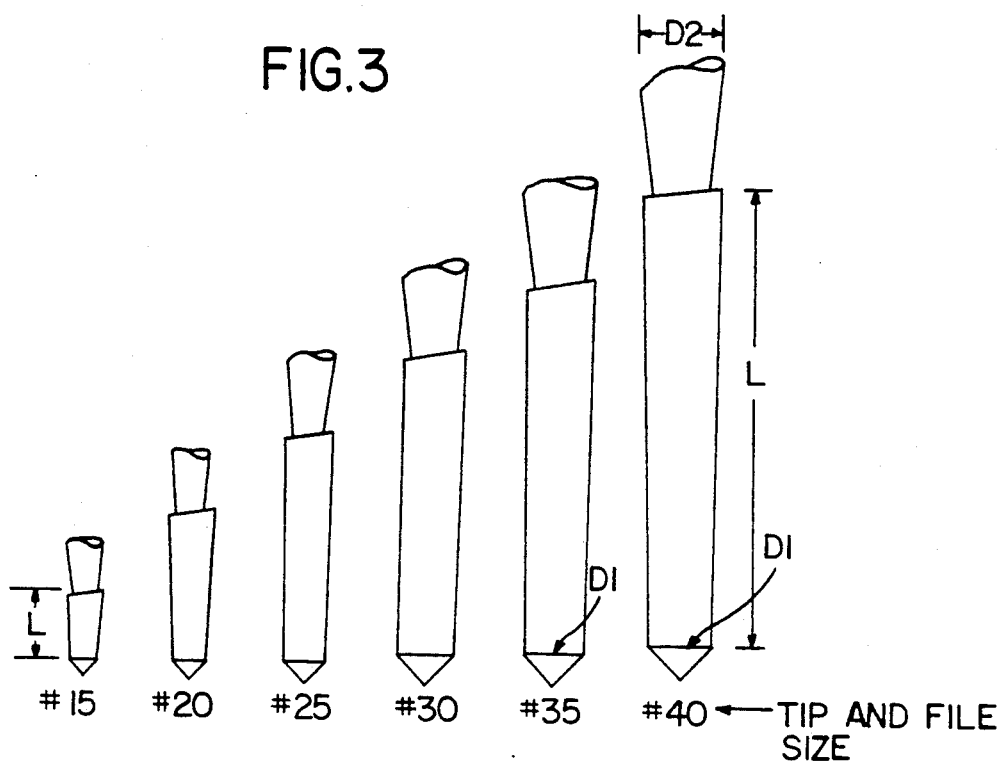
FIG. 3 illustrates the graduated-smooth sided pilot of one variation of apex file set of the present invention the smooth sided pilots with the pointed tips increase in diameter and length between the respective files.; and is a schematic of a set of files of this invention with increasing diameters and lengths to the fourth file, and increasing lengths of the files thereafter.

It is to be noted that the drawings are are drawn to different scales for length L and diameter D.

DESCRIPTION OF THE PREFERRED EMBODIMENTS

Referring now to FIGS. 1 and 2, there are shown prior art files 10 and 12 that differ from one another primarily in the method used to furnish their cutting edges. In FIG. 1, the cutting edges of the "K" apical file 10 are helical, while in FIG. 2 the "cascaded" or "telescopic" cutting edges of the Hedstroem "H" file 12 are at a shallow angle to the file axis.

All files 10 and 12 would have a shank portion 14 and a tapered portion 16. Cutting edges 18 and 20 are provided for the "K" apical file 10 and the Hedstroem file 12, respectively. A safe end 22 is provided for both files 10 and 12.

It is to be noted that in FIGS. 1 and 2, all axial dimensions and point angles are the same for all sizes of files 10 and 12. Point and shank diameters vary as follows:

| File NO. | Dia. D1 | Dia. D2 |
|---|---|---|
| #15 | .15 | .37 |
| #20 | .20 | .52 |
| #25 | .25 | .57 |
| #30 | .30 | .62 |
| #35 | .35 | .67 |
| #40 | .40 | .72 |

(Dimensions are millimeters)

Figure 4:
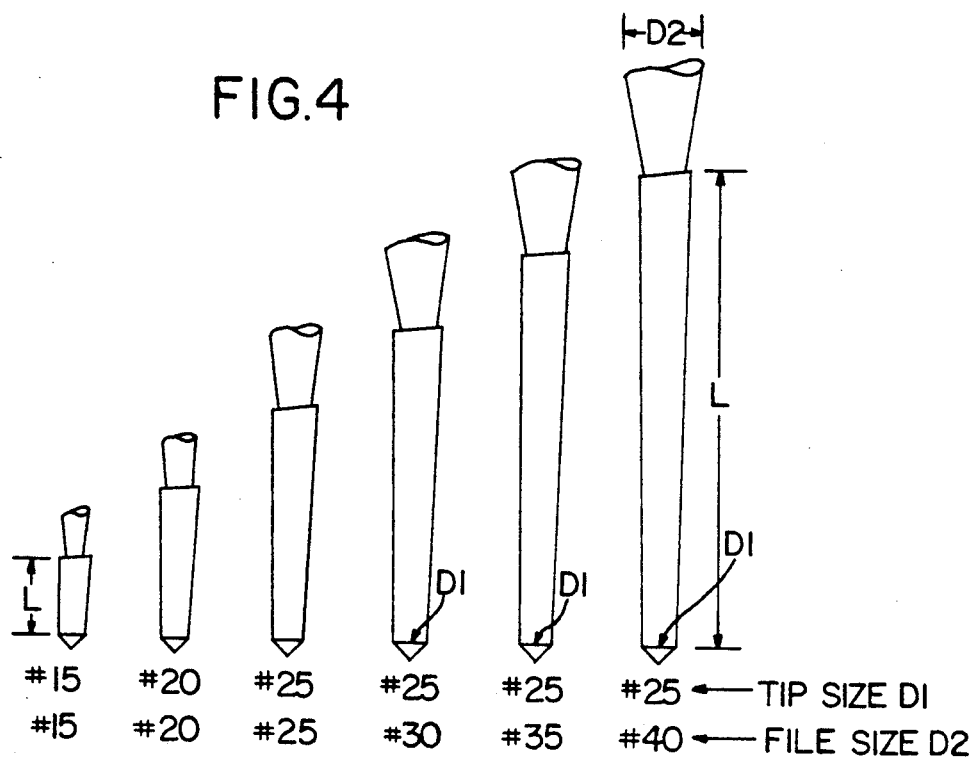

Referring now to FIG. 3 there is illustrated one variation set of the graduated smooth sided pilot with a pointed tip 24 of the file 30 of the instant invention, while FIG. 4 shows a second variation set of the file. The remainder of the file 30 would be much as shown in either FIG. 1 or FIG. 2.

The graduated length smooth sided pilot with a pointed up 24 of the apex file 30 of FIG. 3 vary as follows.

| File No. | Point Length |
|----------|--------------|
| #15 | .5 mm |
| #20 | .1 mm |
| #25 | 1.5 mm |
| #30 | 2.0 mm |
| #35 | 2.5 mm |
| #40 | 3.0 mm |

(Dimensions are metric)

To avoid forcing debris and filling material out the apex and in order to create a proper apical stop of proper retention and resistance, the file 30 of FIG. 3 is necessary to achieve this critical phase of root canal preparation. The apex file 30 of this invention solves this problem. This would equally apply to the variation set 30A of files 24A of FIG. 4.

The smooth sided pilot with a panted tip endodontic K-type file, K-type reamer, H-type Hedstroem instrument, S-type file and R-type file (rhomboid) are provided, with the pilot end of the file 30 measured from D1 will be from 0.5-3 mm before the cutting edges are developed on all types of endodontic cutting instruments and on all sizes from 0.5-40.

The pilot end of the apex file 30 can be incrementally increased based upon the increasing size of the instruments, such as #15=0-1mm pilot end; #20=0.5-1.5 mm pilot end; and #25=1-2 mm pilot end. For example, #15=0.5 mm pilot end, #20=1 mm pilot end, #25=3 mm pilot end, etc. This is to be used for ease with the step back preparation technique.

The smooth sided ended pilot apex file #15 has the ability to act as pathfinder into the canal without damaging the apex portion during this phase.

As can be readily understood from the foregoing description of the invention, the present structure can be configured in different modes to provide a device for playing a plurality of games.

Accordingly, modifications and variations to which the invention is susceptible may be practiced without departing from the scope and intent of the appended claims.

What is claimed is:

1. A set of endodontic files for use with a tooth, comprising, a set of files, with each said file having a smooth sided probe with a pointed tip to facilitate penetration and cutting through blockages and debris of said tooth, each said file also having a cutting edge along the longitudinal axis adjacent to said smooth sided probe, and with each said file in said set of files having a different combination of length of said smooth sided probe and width of said smooth sided probe across the diameter at the base of said pointed tip of said smooth sided probe and of files including files with varying diameters at the base of said pointed tip of said smooth sided probe.

2. A set of endodontic files for use with a tooth as recited in claim 1, wherein the diameters at said base of said pointed tip of the probe vary between each said file in said set of files and the length of said smooth sided probe remains constant between each said file in set of files wherein said pointed tip of said probe of each file has the same angle for each file in said set of files.

3. A set of endodontic files for use with a tooth as recited in claim 2, wherein the diameters of said files vary between each file in said set of files with the diameter at said base of said pointed tip varying from 0.15 mm to 0.4 mm.

4. A set of endodontic files for use with a tooth as recited in claim 3, wherein said length of said length of said smooth sided probe is between 0.5 mm and 1.5 mm and is the same for each file in said set of files.

5. A set of endodontic files for use with a tooth as recited in claim 1, wherein the axial dimensions vary between each file in said set of files and said length of said smooth sided probe varies between each said file in said set of files and wherein the pointed tip of said smooth sided probe of each file has the same angle for each file in said set of files.

6. A set of endodontic files for use with a tooth as recited in claim 5, wherein the diameters at said abase of said pointed tip of said smooth sided probe in the axial dimensions vary between 0.15 mm and 0.25 mm and the length of said smooth sided probe varies between 0.5 mm and 3 mm.

7. A set of endodontic files for use with a tooth as recited in claim 6, wherein the diameter of the cutting edge portion varies between size #15 and size #40.

8. A set of endodontic files for use with a tooth as recited in claim 7, wherein for each succeeding larger file larger than size #25, said pilot portion remains #25 (0.25 mm diameter tip) and said cutting edge portion increases in diameter between successive files by incremental steps of 0.05 mm at the junction of said smooth probe portion and said cutting edge portion of said file so that the side of the file increases in a step between the probe and cutting portions of said file.

9. A set of endodontic files for use with a tooth as recited in claim 1, wherein each said file has a shank portion and a tapered portion, with the cutting edge portion of each said file in each said set of files being positioned on said tapered portion adjacent to said cutting edge portion.

* * * * *